United States Patent
Novatzky et al.

(10) Patent No.: US 7,634,121 B2
(45) Date of Patent: Dec. 15, 2009

(54) METHOD AND SYSTEM FOR RULE-BASED COMPARISON STUDY MATCHING TO CUSTOMIZE A HANGING PROTOCOL

(75) Inventors: Benjamin D. Novatzky, Oak Park, IL (US); Richard W. I. Yarger, Berkeley, IL (US); Muthu Venkatesh Muthuraj, Kenosha, WI (US)

(73) Assignee: General Electric Company, Schenectady, NY (US)

( * ) Notice: Subject to any disclaimer, the term of this patent is extended or adjusted under 35 U.S.C. 154(b) by 819 days.

(21) Appl. No.: 11/070,104

(22) Filed: Mar. 1, 2005

(65) Prior Publication Data

US 2006/0239573 A1  Oct. 26, 2006

(51) Int. Cl.
*G06K 9/00* (2006.01)
*G06K 9/36* (2006.01)

(52) U.S. Cl. .................... 382/128; 382/239
(58) Field of Classification Search ......... 382/128–132, 382/317, 329; 600/407; 606/155; 709/225, 709/204; 378/207; 705/2–4; 707/10, 100; 704/270.1; 341/51; 358/426.02–426.11
See application file for complete search history.

(56) References Cited

U.S. PATENT DOCUMENTS

| | | | | |
|---|---|---|---|---|
| 5,835,618 A | * | 11/1998 | Fang et al. | 382/132 |
| 6,326,962 B1 | * | 12/2001 | Szabo | 715/762 |
| 6,574,629 B1 | * | 6/2003 | Kaufman et al. | 707/10 |
| 6,661,925 B1 | * | 12/2003 | Pianykh et al. | 382/239 |
| 6,711,297 B1 | * | 3/2004 | Chang et al. | 382/240 |
| 6,771,822 B1 | * | 8/2004 | Brackett | 382/232 |
| 6,785,410 B2 | * | 8/2004 | Vining et al. | 382/128 |
| 7,016,952 B2 | * | 3/2006 | Mullen et al. | 709/224 |
| 7,133,546 B2 | * | 11/2006 | Dehmeshki et al. | 382/128 |
| 7,222,079 B1 | * | 5/2007 | Seare et al. | 705/3 |
| 7,234,064 B2 | * | 6/2007 | Menschik et al. | 713/193 |
| 7,418,120 B2 | * | 8/2008 | Weiner et al. | 382/128 |
| 2001/0029334 A1 | * | 10/2001 | Graumann et al. | 600/437 |
| 2003/0016850 A1 | * | 1/2003 | Kaufman et al. | 382/128 |
| 2003/0046114 A1 | * | 3/2003 | Davies et al. | 705/3 |
| 2004/0034550 A1 | * | 2/2004 | Menschik et al. | 705/3 |
| 2007/0232868 A1 | * | 10/2007 | Reiner | 600/300 |

\* cited by examiner

*Primary Examiner*—Samir A Ahmed
*Assistant Examiner*—Mehdi Rashidian
(74) *Attorney, Agent, or Firm*—McAndrews, Held & Malloy, Ltd.; Peter J. Vogel; Michael A. Dellapenna

(57) ABSTRACT

The present invention provides a method for presenting at least one medical imaging study in a Picture Archiving and Communication System ("PACS"). The method includes selecting at least one comparison imaging study from a plurality of historical imaging studies by comparing at least one image data attribute associated with a current imaging study with at least one image data attribute associated with each of the plurality of historical studies. The relevant historical studies are automatically selected as comparison imaging studies.

28 Claims, 4 Drawing Sheets

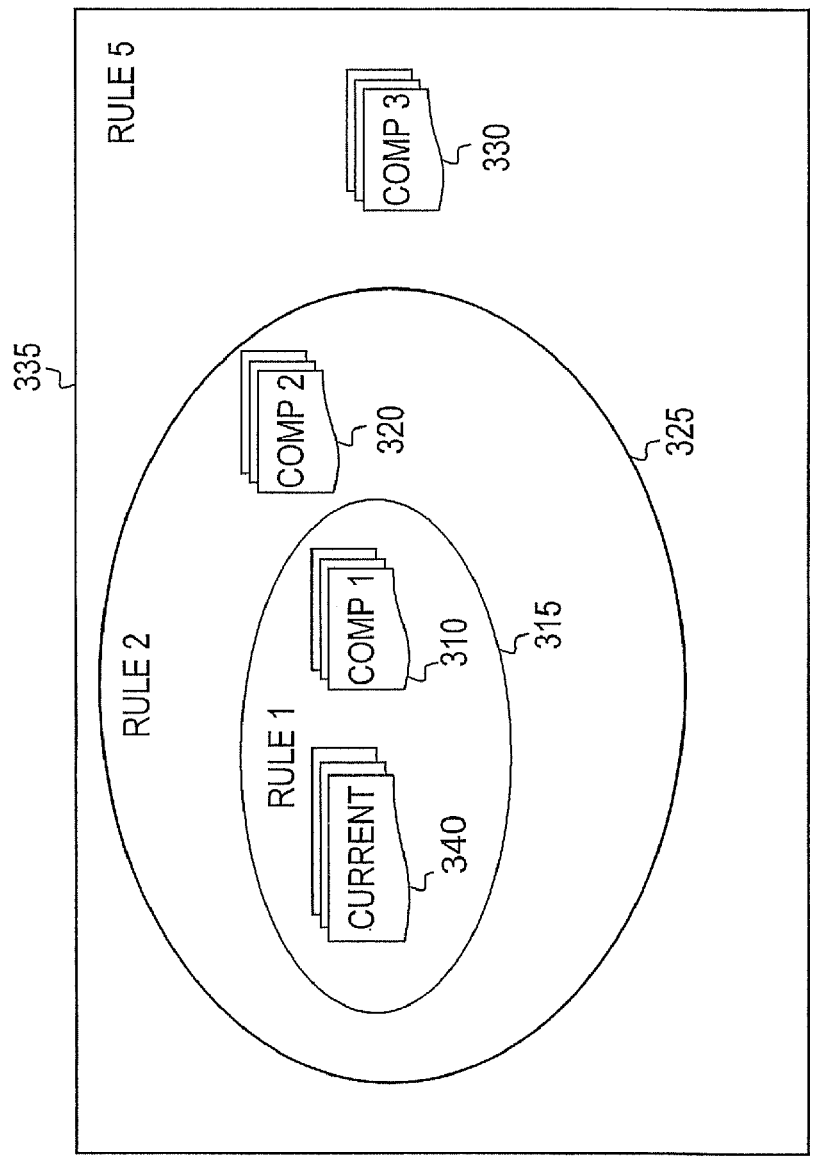

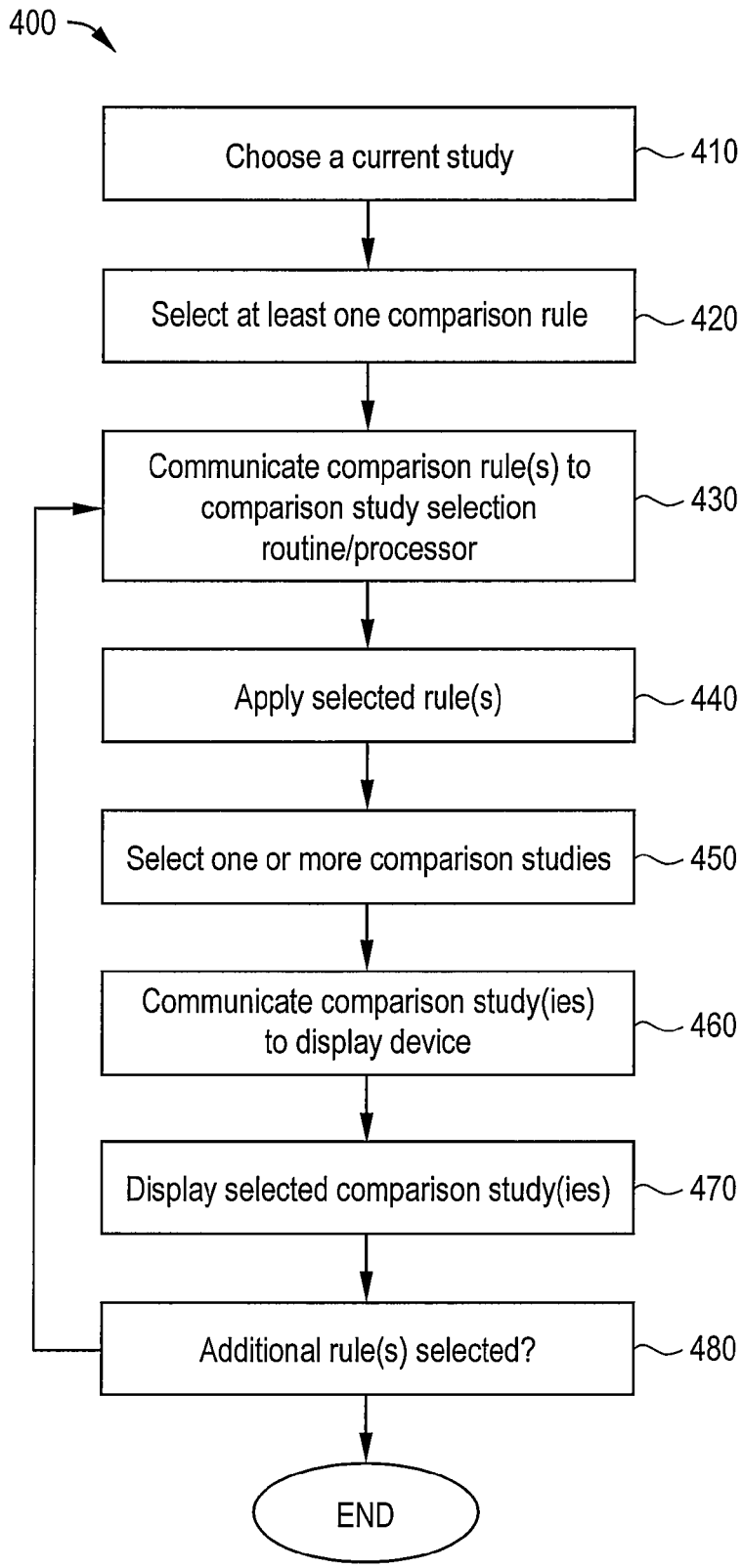

METHOD AND SYSTEM FOR RULE-BASED COMPARISON STUDY MATCHING TO CUSTOMIZE A HANGING PROTOCOL

BACKGROUND OF THE INVENTION

The present invention generally relates to an improvement in the selection and presentation of medical imaging studies. Specifically, the present invention relates to an improved method and system for rule-based comparison study matching to customize a hanging protocol.

Picture archiving and communication systems ("PACS") connect to medical diagnostic imaging devices and employ an acquisition gateway (between the acquisition device and the PACS), storage and archiving units, display workstations, databases, and sophisticated data processors. These components are integrated together by a communication network and data management system. A PACS has, in general, the overall goals of streamlining health-care operations, facilitating distributed remote examination and diagnosis, and improving patient care.

A typical application of a PACS system is to provide one or more medical images for examination by a medical professional. For example, a PACS system can provide a series of x-ray images to a display workstation where the images are displayed for a radiologist to perform a diagnostic examination. Based on the presentation of these images, the radiologist can provide a diagnosis. For example, the radiologist can diagnose a tumor or lesion in x-ray images of a patient's lungs.

A series or sequence of a plurality of medical images is an imaging study. In general, an imaging study that is the most recent imaging study of a patient or is the imaging study currently being examined by a radiologist will be referred to as a current imaging study.

In order to properly diagnose a current imaging study, a radiologist must examine one or more previously acquired images of the same patient and compare these images to images of a current study. An imaging study that includes two or more previously acquired images is a historical imaging study. Furthermore, a historical imaging study whose images are relevant for comparing with the images of a current imaging study is a comparison imaging study. For example, images that are associated with or display the same anatomy are relevant for comparison purposes.

The images of an imaging study are displayed in a particular spatial layout and/or temporal sequence. In other words, the images may be displayed in certain positions on a display device relative to each other (a spatial layout, for example). The images may also be displayed in a certain ordered sequence by displaying image A first, followed by image B, followed by image C, and so on (a temporal sequence, for example). The spatial and/or temporal presentation of images is directed by a set of display rules. A display rule may include a set of instructions stored on a computer-readable media that direct the presentation of images on a display workstation. A set of display rules is known as a hanging protocol. In general, a hanging protocol is a series of display rules that dictate the spatial and/or temporal layout and presentation of a plurality of images.

Current hanging protocols provide for the display of comparison imaging studies on a display workstation. For example, current complex hanging protocols allow a user or radiologist to specify how many comparison imaging studies to automatically populate onto a display at a display workstation and/or the layout of the images in the comparison imaging studies. However, the comparison imaging studies that are automatically displayed are the most recent comparison imaging studies. While this may assist some radiologists in their examinations of imaging studies, the most recent comparison studies are not always the most relevant imaging studies for a particular diagnosis.

For example, a radiologist may wish to compare images from a current study with a previous imaging study that was acquired using the same or similar imaging modality, imaging procedure, or radiologist, or that includes images of the same or similar anatomies. However, current hanging protocols do not provide for this flexibility. Instead, a radiologist must spend a considerable amount of time manually searching through the most recent comparison studies populated by a hanging protocol in order to find the most relevant and helpful comparison study(ies). A need therefore exists for a more flexible method of adjusting hanging protocols to automatically select the comparison study(ies) of greatest interest to a radiologist. Meeting such a need can result in several improvements in current PACS, such as increased efficiency, improved diagnosis times in emergency situations, increased productivity, and increased flexibility.

The efficiency of current PACS may be increased as a user or radiologist does not need to spend as much time searching for desired comparison studies. This is especially helpful in situations where a patient may have tens or hundreds of historical or comparison studies. In addition, the efficiency of a PACS is enhanced by the fact that the comparison studies may be automatically displayed to the user.

Similarly, as the efficiency of finding a desired comparison study may be increased, the amount of time required for a proper diagnosis can decrease. Such a decrease in diagnosis time can be critical in emergency-type scenarios where any extra time may jeopardize patient health or survival.

The productivity of a user may be improved upon as the user spends less time searching and setting up desired comparison studies. In addition, users can more easily ignore comparison studies that are not of interest to the user.

Finally, the flexibility of a PACS may be increased as a user may have the ability to configure one or more rules by which a hanging protocol selects one or more comparison studies. The user may also be able to configure these rules for each diagnosis.

BRIEF SUMMARY OF THE INVENTION

The present invention provides a method for presenting at least one medical imaging study in a Picture Archiving and Communication System ("PACS"). The method includes selecting at least one comparison study from a plurality of historical studies by comparing at least one image data attribute associated with a current study with at least one image data attribute associated with each of the plurality of historical studies. The current study and each of the plurality of historical studies includes at least one image.

The present invention also provides a computer-readable storage medium including a set of instructions for a computer. The instructions include a rule selection routine and a comparison study selection routine. The rule selection routine is configured to monitor a selection of at least one rule from a plurality of rules. The rules are capable of being used to compare at least one image data attribute associated with a current study with at least one image data attribute associated with each of a plurality of historical studies. The current study and the plurality of historical studies each include at least one image. The comparison study selection routine is configured to select at least one comparison study from the plurality of historical studies by comparing at least one image data attribute of the current study with at least one image data attribute associated with each of the plurality of historical studies in accordance with at least one rule.

The present invention also provides a system for presenting at least one medical imaging study at a display workstation in a Picture Archiving and Communication System ("PACS"). The system includes a computer-readable storage medium and a comparison study selection processor. The storage medium is configured to store a plurality of rules. Each of the rules is capable of being used to compare at least one image data attribute associated with a current study with at least one image data attribute associated with each of a plurality of historical studies. The current study and the plurality of historical studies each include at least one image. The comparison study selection processor is configured to select one or more comparison studies from the plurality of historical studies by comparing at least one image data attribute associated with the current study with at least one image data attribute associated with at least one historical study in accordance with at least one of the plurality of rules.

BRIEF DESCRIPTION OF SEVERAL VIEWS OF THE DRAWINGS

FIG. 3 illustrates an example of applying three comparison rules in order to customize a hanging protocol in accordance with an embodiment of the present invention.

FIG. 4 illustrates a flowchart for a method 400 for rule-based comparison study matching to customize a hanging protocol in accordance with an embodiment of the present invention.

Figure 1:
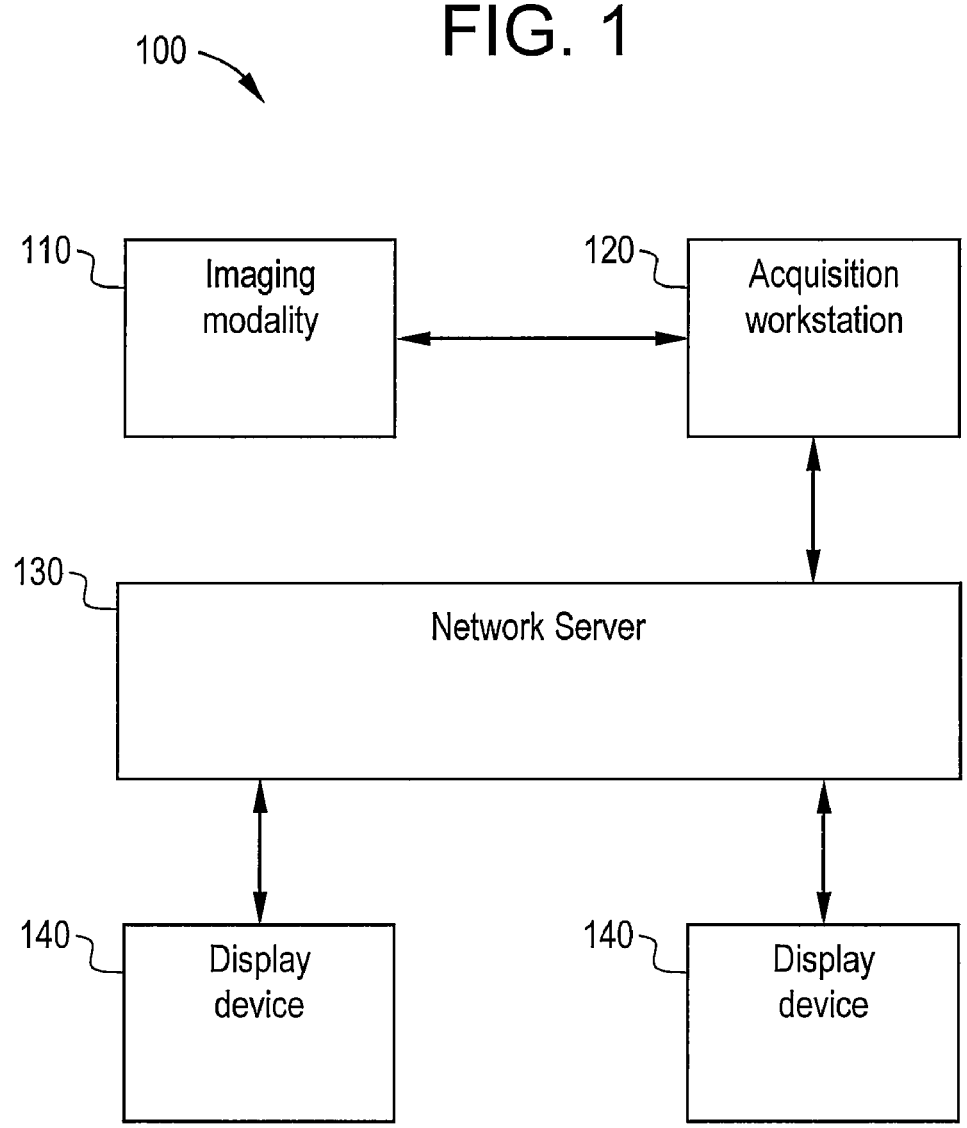
FIG. 1 illustrates an exemplary PACS system in accordance with an embodiment of the present invention.

The foregoing summary, as well as the following detailed description of certain embodiments of the present invention, will be better understood when read in conjunction with the appended drawings. For the purpose of illustrating the invention, certain embodiments are shown in the drawings. It should be understood, however, that the present invention is not limited to the arrangements and instrumentality shown in the attached drawings.

DETAILED DESCRIPTION OF THE INVENTION

FIG. 1 illustrates an exemplary PACS system 100 in accordance with an embodiment of the present invention. PACS system 100 includes an imaging modality 110, an acquisition workstation 120, a network server 130, and two display devices 140. While system 100 is illustrated in FIG. 1 as including a single imaging modality 110, a single acquisition workstation 120, a single network server 130, and two display devices 140, system 100 can include any number of imaging modalities 110, acquisition workstations 120, network servers 130, and/or display devices 140. In other words, no embodiment of the present invention is in any way limited to the illustration of system 100 as illustrated in FIG. 1.

Imaging modality 110 is capable of communicating with acquisition workstation 120. Acquisition workstation 120 is capable of communicating with imaging modality 110 and server 130. Server 130 is capable of communicating with acquisition workstation 120 and display devices 140. Display devices 140 are capable of communicating with server 130. In another embodiment of the present invention, display devices 140 may also communicate directly with acquisition workstation 120.

In operation, imaging modality 110 obtains one or more images of a patient anatomy. Imaging modality 110 can include any device capable of capturing an image of a patient anatomy, such as a medical diagnostic imaging device. For example, imaging modality 110 can include am x-ray imager, ultrasound scanner, magnetic resonance imager, computed radiography/tomography imager, nuclear imager, or the like. Image data representative of the image(s) is communicated between imaging modality 110 and acquisition workstation 120. The image data can be communicated electronically over a wired or wireless connection, for example.

Acquisition workstation 120 may apply one or more pre-processing functions to the image data. The preprocessing functions may be employed to prepare the image(s) for viewing on one or more display devices 140 and/or to prepare the image(s) for storage at one or more of display devices 140 and server 130. For example, acquisition workstation 120 may convert raw image data into a DICOM standard format or attach a DICOM header. In another example, a preprocessing function may include contrast or frequency preprocessing of an image.

Acquisition workstation 120 may attach or associate image data attributes with the image(s). An image data attribute can include any electronically communicable data representative of information relevant to the image(s), patient, patient anatomy, and/or medical or imaging procedure, for example. Exemplary image data attributes include data representative of an imaging procedure, one or more DICOM tag(s) and/or one or more patient anatomies or mapped anatomies.

An image data attribute representative of an imaging procedure can include data representative of the procedures used to obtain the image(s) (to which the image data attribute is attached or associated). An imaging procedure can include a sequence of imaging steps used to obtain one or more images. For example, an imaging procedure can include the insertion of a contrast agent in a patient and then taking one or more images of the patient anatomy that includes the contrast agent. In another example, an imaging procedure may include the acquisition of one or more images without using any sort of contrast agent.

An imaging procedure may include the taking of one or more images of a certain patient anatomy. For example, an imaging procedure may identify which patient anatomy (such as a patient's head, neck or chest) is featured or shown in one or more images, for example.

An imaging procedure may also include the particular imaging modality used to obtain one or more images and/or particular type or class of imaging modality used to obtain one or more images. A particular imaging modality may be a certain or particular imaging modality device of a plurality of imaging modality devices. In another example, a particular type or class of imaging modality may be a C-arm x-ray imaging device, magnetic resonance ("MR") imaging device, etc.

An imaging procedure may also include a representation of a user that employed an imaging modality to obtain the image(s). For example, an imaging procedure may include a representation of an identity of a radiologist who used an MR imaging device to obtain the image(s).

An image data attribute may include data representative of one or more DICOM tags. A DICOM tag may be attached to or associated with image data by imaging modality 110 and/or acquisition workstation 120. A DICOM tag may include any data specified by the DICOM Standard or any custom data allowed for by the DICOM Standard. For example, a DICOM tag may include image display data (e.g., (7FE0, 0010) Pixel Data), image data characteristics (e.g., (0028, 0002) Samples Per Pixel, (0028,0004) Photometric Interpretation), image capture characteristics (e.g., (0018,1050) Spatial Resolution, (0018,5101) View Position), anatomy data (e.g., (0018,0015) Body Part Examined), imaging device data (e.g., (0008,0060) Modality, (0008,1090) Manufacturer's Model Name), study-specific data (e.g., (0008,0020) Study Date, (0008,0030) Study Time), patient-specific data (e.g., (0010,0010) Patient's Name, (0010,0030) Patient's Birth Date), or any other data allowed for by the DICOM Standard.

An image data attribute may include data representative of a patient anatomy. Such data may include one or more mapped body parts. A mapped body part is any body part or anatomy featured in the image(s). An image data attribute that includes a mapped body part may be input by a user of system 100. For example, a radiologist may list or statically map the body part(s) or anatomy(ies) to be examined in an imaging procedure and/or featured in one or more images. Such a list may be attached to or associated with the image(s) as an image data attribute.

The image data (and associated image data attribute(s)) may then be communicated between acquisition workstation 120 and server 130. The image data may be communicated electronically over a wired or wireless connection.

In another embodiment of the present invention, as described above, image data (and associated image data attribute(s)) may be directly communicated between acquisition workstation 120 and one or more display devices 140. The image data and image data attribute(s) may be communicated over a wired or wireless connection.

Server 130 can include any computer-readable storage and retrieval device that is accessible over an intranet or over the Internet. Server 130 can include a computer-readable storage medium suitable for storing the image data for later retrieval and viewing at a display device 140. Server 130 can also include a computer-readable storage medium suitable for storing one or more comparison rules, as described in more detail below.

Images (and associated image data attributes) and/or one or more comparison rules may be communicated between server 130 and one or more display devices 140. The image data and associated image data attribute(s) and/or comparison rules may be communicated over a wired or wireless connection or transferred on a physical media, such as magnetic tape.

One or more display devices 140 are capable of communication with or configured to communicate with server 130. A display device 140 can include any device capable of displaying an imaging study. An imaging study is a group of one or more images. An imaging study may be used in a PACS system to make a diagnosis based on one or more images. For example, as described above, a radiologist using system 100 may employ a display device 140 to analyze a series of images of a patient's lungs. The radiologist may use the images to determine whether the patient's lungs include a tumor.

As described above, display devices 140 can include any device capable of presenting an imaging study. For example, one exemplary display device 140 includes a display workstation in a PACS system. A display workstation 140 can include a general purpose processing circuit, a network server 130 interface, a software memory, an input device (such as a keyboard, mouse, stylus, microphone, etc.) and an output device (such as an image display monitor or computer monitor), for example. The network server 130 interface may be implemented as a network card connecting to a TCP/IP based network, but may also be implemented as a parallel port, USB, or FireWire interface, for example. While one exemplary display device 140 is described, this example should not be construed as limiting the present invention to just one display device 140. As described above, a display device 140 includes any device capable of presenting or displaying an imaging study to a user. Therefore, a display device 140 may also be embodied in a wireless display device, for example.

As described above, display devices 140 may retrieve or receive image data (for example, an imaging study) from server 130 for display to one or more users. For example, a display device 140 may retrieve or receive an imaging study that includes a computed radiography ("CR") image of a patient's chest. A radiologist may then examine the image as displayed on a display device for any objects of interest such as, tumors, lesions, etc.

Display devices 140 may also be capable of retrieving/receiving or configured to retrieve/receive one or more hanging protocols from server 130. For example, a default hanging protocol may be communicated to display workstation 140 from server 130.

Display devices 140 may present one or more imaging studies according to a hanging protocol. As described above, a hanging protocol is a set of display rules for presenting, formatting, and otherwise organizing images on a display device of a display device 140. A display rule is a convention for presenting one or more images in particular temporal and/or spatial layout or sequence. For example, a hanging protocol may include a set of computer-readable instructions (or display rules, for example) that direct a computer to display a plurality of images in certain locations on a display device and/or display the plurality of images in a certain sequence or order. In another example, a hanging protocol may include a set of computer-readable instructions that direct a computer to place a plurality of images in multiple screens and/or viewing areas on a display device 140. In general, a hanging protocol may be employed to present a plurality of images for a diagnostic examination of a patient anatomy featured in the images.

A hanging protocol may direct, for example, a display device 140 to display an anterior-posterior ("AP") image adjacent to a lateral image of the same patient anatomy. In another example, a hanging protocol may direct display device 140 to display the AP image before displaying the lateral image (in other words, prior in time). In general, a hanging protocol dictates the spatial and/or temporal presentation of a plurality of images in one or more imaging studies at a display device 140. A hanging protocol may also be used to select images and/or imaging studies to present at display device 140.

As described above, one or more comparison rules may be communicated between server 130 and one or more display devices 140. A comparison rule is a rule that compares at least one image data attribute attached to or associated with a current imaging study with at least one image data attribute attached to or associated with at least one historical imaging study in order to select one or more comparison imaging studies.

As described above, a current study is an imaging study that is currently being examined or analyzed by a user at a display device 140 of a PACS system 100 and a historical study is an imaging study that includes previously acquired images of one or more patient anatomies.

A historical or previous imaging study that is relevant for comparison purposes is known as a comparison study. Current hanging protocols do allow for a user to retrieve a comparison study. However, these hanging protocols typically just deliver the most recent comparison study or a list of all recent comparison studies available to a user. These hanging protocols do not allow for the comparison of one or more image data attributes in order to deliver the most relevant comparison imaging study(ies).

Typically, the user compares a current study with a previous imaging study in accordance with a hanging protocol. A comparison study may be relevant to a current imaging study if a user wishes to compare the current study with the comparison study in order to determine whether any changes have occurred in a patient's anatomy imaged in both the current and comparison studies, for example. Or, a user may wish to compare the current study with a comparison study in order to simply obtain additional information (obtainable by images taken with a different imaging procedure, for example) concerning a patient anatomy that is not discernable from the current study, for example. In another example, by comparing a comparison study with a current study, a user may be able to determine the effect of a contrast (or lack thereof) on an anatomy.

Figure 2:
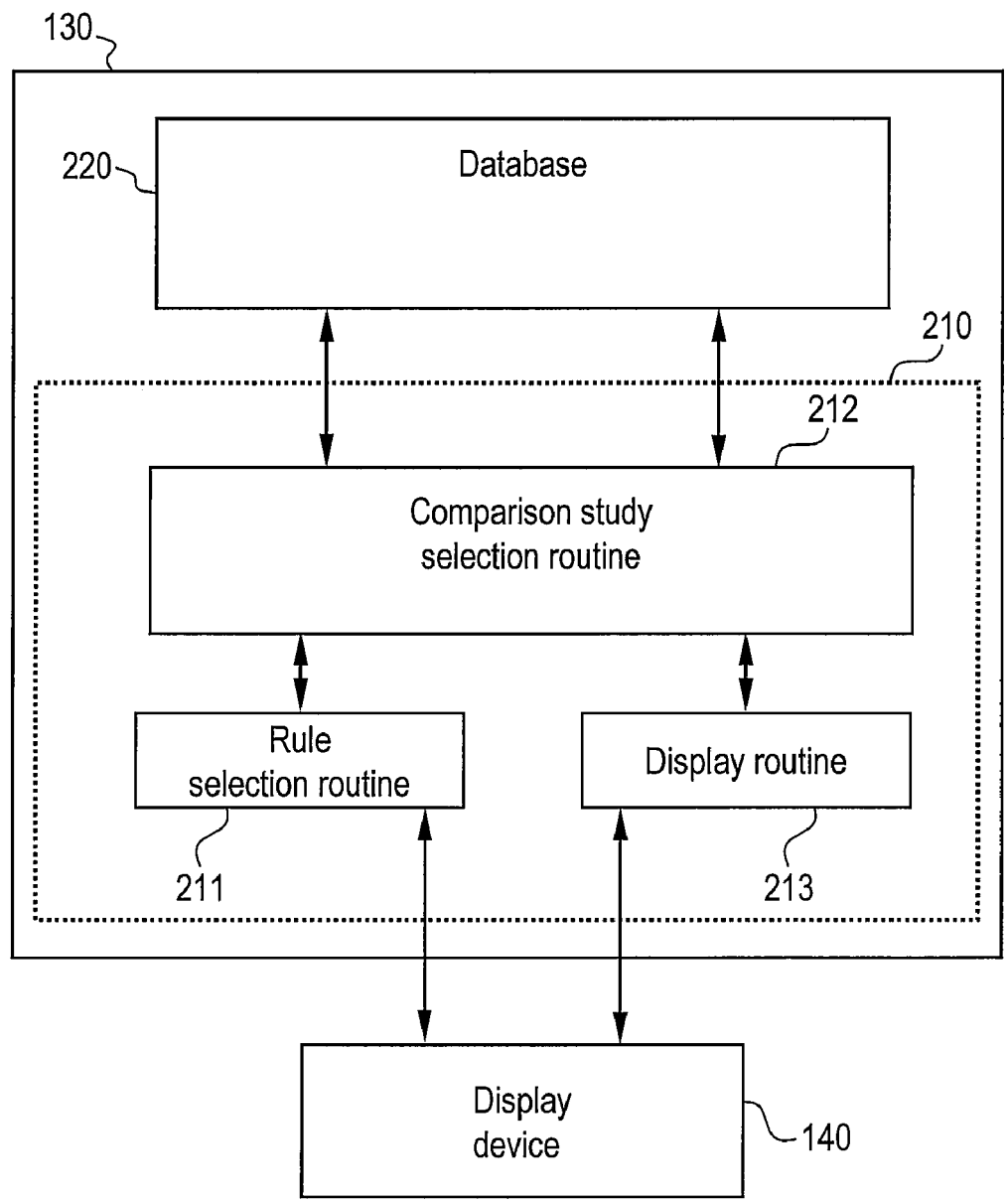
FIG. 2 illustrates server 130 in accordance with an embodiment of the present invention.

FIG. 2 illustrates server 130 in accordance with an embodiment of the present invention. Server 130 includes a computer-readable storage medium 210 and a database 220. Storage medium 210 includes a set of instructions (211 through 213) for a computer. The instructions (211 through 213) may be embodied in one or more software applications stored on storage medium 210, for example. In another embodiment of the present invention, the instructions (211 through 213) may reside on different storage mediums 210 on the same server 130 or on different servers 130. The instructions (211 through 213) include a rule selection routine 211, a comparison study selection routine 212, and a display routine 213. Rule selection routine 211 is capable of communicating with or is configured to communicate with display device 140 and comparison study selection routine 212. Comparison study selection routine 212 is capable of communicating with or is configured to communicate with rule selection routine 211, database 220, and display routine 213. Display routine 213 is capable of communicating with or is configured to communicate with comparison study selection routine 212 and display device 140.

In another embodiment of the present invention, any one or more of a rule selection routine 211, a comparison study selection routine 212, and a display routine 213 may be embodied in software running on a shared or dedicated computer processor. For example, rule selection routine 211 may be embodied as a rule selection processor 211. Similarly, comparison study selection routine 212 may be embodied as a comparison study selection processor 212 and display routine 213 may be embodied as a display processor 213.

Database 220 includes any computer-readable storage medium. Database 220 may be used to store any one or more of image data, image data attributes, imaging studies (current studies and/or historical studies), hanging protocols, rules (as described above), or any other information that may be stored on computer-readable media. While server 130 is illustrated with only one database 220, in accordance with the present invention, server 130 may include any number of databases 220. For example, server 130 may include a plurality of databases 220, each dedicated to the storage of a different type of data.

In another embodiment of the present invention, one or more of rule selection routine 211, comparison study selection routine 212, display routine 213, and database 220 may reside on display device 140. For example, one or more software applications may include one or more of routines 211, 212, and 213 and reside on a memory of display device 140. In another example, database 220 may be embodied as a computer-readable storage medium in display device 140. However, the functions performed by each of routines 211, 212, 213 and database 220 do not change when any one or more of routines 211, 212, 213 and/or database 220 reside on display device 140. In other words, the following discussion of how each routine 211, 212, 213 and database 220 work in accordance with embodiments of the present invention applies to each routine 211, 212, 213 and database 220 whether each resides on server 130 or display device 140.

In operation, a user employing display device 140 selects a current imaging study to be displayed on display device 140. The current imaging study may be communicated from server 130 to display device 140 or from acquisition workstation 120 to display device 140.

A user may select one or more comparison rules to customize the hanging protocol (as described in more detail below). In accordance with an embodiment of the present invention, a hanging protocol may include one or more comparison rules configured to deliver the most relevant comparison study(ies) to a user. In general, a user may select one or more rules (stored at server 130 or display device 140) that dictate which image data attribute(s) of a current study is/are to be compared to one or more historical studies in order to select or filter one or more comparison studies from the historical studies. In this way, a rule of a hanging protocol may act as a filter to prevent all non-relevant historical studies from being communicated to a user.

The user may select one or more rules from a list of rules graphically displayed on display device 140 using an input device. Once the user selects the rule(s) (thereby making a rule selection), the rule selection is communicated from display device 140 to rule selection routine 211 of server 130.

Rule selection routine 211 receives the rule selection from device 140. Rule selection routine 211 communicates the rule selection to comparison study selection routine 212. Once comparison study selection routine 212 receives the rule selection, comparison study selection routine 212 applies the selected rule(s) to a plurality of historical studies.

In another embodiment of the present invention, one or more rules may be selected by a user pre-configuring a hanging protocol for a particular procedure or set of procedures to automatically apply a rule or set of rules whenever an imaging study of the particular procedure(s) is displayed. For example, a user may configure a hanging protocol to automatically select a set of rules (to be applied to a plurality of historical studies) whenever a current imaging study (that was obtained with a given imaging procedure or set of procedures) is viewed on display device 140.

Comparison study selection routine 212 applies a comparison rule by examining one or more relevant image data attributes of a plurality of historical studies stored at database 220. An image data attribute is relevant to a comparison rule if the image data attribute is of the same type or class of image data attribute examined by the comparison rule. Comparison study selection routine 212 applies a comparison rule by determining which historical studies include one or more image data attributes that satisfy or match an image data attribute of the comparison rule. If a historical study includes an image data attribute that satisfies a comparison rule, then that historical study is selected as a comparison study by comparison study selection routine 212 (as described in more detail below, more than one comparison study may be selected). The selected comparison study(ies) is(are) then communicated from database 220 to display routine 213.

The following examples provide exemplary comparison rules and their application to select/filter one or more comparison studies from a plurality of historical studies. In a first example, a first comparison rule may require that an imaging procedure used to obtain images in one or more comparison studies match, or be equivalent to, an imaging procedure used to obtain images in the current study. For example, a current study was created using imaging procedure B and the following historical studies were created with the listed imaging procedure:

| Historical Study Number | Imaging Procedure |
|---|---|
| 1 | C |
| 2 | A |
| 3 | D |
| 4 | B |
| 5 | A |
| 6 | B |

If the first comparison rule requires that the imaging procedure of the current study match the imaging procedure of a historical study in order for that historical study to be selected as a comparison study, then upon application of the rule to the historical studies listed in the table, historical studies numbered 4 and 6 would be selected as comparison studies.

In a second example, a second comparison rule may require that one or more DICOM tags associated with a historical study match any DICOM tags associated with the current study in order for that historical study to be selected as a comparison study. For example, the second comparison rule may require that a "Body Part Examined" DICOM tag of a historical study match any "Body Part Examined" DICOM tag of the current study in order for that historical study to be selected as a comparison study and communicated to a user. While a "Body Part Examined" DICOM tag is used in this example, any DICOM tag may be used. For example, a current study includes "Body Part Examined" DICOM tags of {A, C} (where A and C each represent a patient anatomy such as a chest or abdomen). The following comparison studies are associated with the listed "Body Part Examined" DICOM tags:

| Historical Study Number | "Body Part Examined" DICOM Tags |
|---|---|
| 1 | A, B |
| 2 | F |
| 3 | B, E |
| 4 | A, C |
| 5 | C |

If the second comparison rule requires that a "Body Part Examined" DICOM tag of a historical study matches any "Body Part Examined" DICOM tag of the current study (in order for that historical study to be selected as a comparison study), then upon application of the rule to the historical studies listed in the table, historical studies numbered 1 (as both studies include "A"), 4 (as both studies include "A" and "C"), and 5 (as both studies include "C") would be selected as comparison studies.

In a third example, a third comparison rule may require that one or more mapped anatomies associated with a historical study match any mapped anatomies in a set of mapped anatomies. For example, the third comparison rule may require that a mapped anatomy of a historical study matches any mapped anatomy in a set of mapped anatomies in order for that historical study to be selected as a comparison study and communicated to a user. For example, a set of mapped anatomies may include mapped anatomies A, C and D (where A, C and D each represent a mapped anatomy such as a head, neck or chest). In general, a set can include one or more mapped anatomies. The following historical studies are associated with the listed mapped anatomies:

| Historical Study Number | Mapped Anatomies |
|---|---|
| 1 | E, G |
| 2 | A |
| 3 | A, C, D |
| 4 | C, D, E |
| 5 | B |

If the third comparison rule requires that a mapped anatomy of a historical study match any mapped anatomy of the set (in order for that historical study to be selected as a comparison study), then upon application of the rule to the historical studies listed in the table, historical studies numbered 2 (as both include "A"), 3 (as both include "A" and "C"), and 4 (as both include "C") would be selected as comparison studies.

In another embodiment of the present invention, the set of mapped anatomies may be a subset of the mapped anatomies associated with a current study. For example, if a current study is associated with mapped anatomies A, C, D, and G, then a subset of mapped anatomies can include any combination of one or more of A, C, D, and G.

In another embodiment of the present invention, a user may define the set or subset of mapped anatomies. For example, a user may select one or more mapped anatomies using an input device.

In a fourth example, a fourth comparison rule may require that an imaging procedure associated with one or more historical studies match any imaging procedures in a set of imaging procedures. The set of imaging procedures may include any one or more imaging procedures that a user uses to match historical imaging studies with a current study. For example, a user may wish to find all historical studies associated with a particular imaging procedure (such as a procedure performed by a particular radiologist, as described above, for example). The user may then use this fourth rule to automatically populate display device 140 with comparison studies obtained by imaging procedures performed by the particular radiologist, for example. However, the set of imaging procedures can include more than one imaging procedure. For example, a set of imaging procedures can be used to select all historical studies (as comparison studies) that include (1) images obtained by a particular C-arm x-ray imaging device and/or (2) images obtained by a particular radiologist.

Continuing with this example, the fourth comparison rule may require that all selected comparison studies have imaging procedures that (1) include images obtained by the particular imaging device ("X") or (2) were obtained by the particular radiologist ("A"). The following historical studies are associated with the listed imaging procedures (including both the device used to obtain the images and the radiologist who performed the procedure):

| Historical Study Number | Imaging Device | Radiologist |
|---|---|---|
| 1 | X | A |
| 2 | Y | C |
| 3 | Z | A |
| 4 | Y | B |
| 5 | X | C |

If the fourth comparison rule requires that any of the imaging procedures of a historical study match any imaging procedures of the set described above (namely "Imaging Device" and "Radiologist") in order for that historical study to be selected as a comparison study, then upon application of the rule to the historical studies listed in the table, historical studies numbered 1 (as comparison study #1 was obtained using Imaging Device X and was performed by Radiologist A), 3 (as comparison study #3 was performed by Radiologist A), and 5 (as comparison study #5 was obtained using Imaging Device X) would be selected as comparison studies.

The set of imaging procedures may be selected by a user from a plurality of previously defined sets of imaging procedures stored on one or more of server 130 and display device 140. In one embodiment, a user may select the set that he or she desires from a displayed list of sets of imaging procedures using an input device.

In another embodiment, the user may customize a set of imaging procedures by defining the imaging procedures in the set. A user may define the imaging procedures in a set by selecting one or more imaging procedures displayed on display device 140 using an input device. For example, a user may select "MR Brain" as an imaging procedure (representing a magnetic resonance imaging procedure of a patient's brain) to be included in the set. In another example, a user may select a plurality of imaging procedures, such as "MR Brain," "MR Brain with contrast," and "MR Brain without contrast." In such an example, any historical studies including images obtained using "MR Brain," "MR Brain with contrast," or "MR Brain without contrast" would be selected as comparison studies.

In a fifth example, a fifth comparison rule may require that one or more mapped anatomies associated with a historical studiy match any mapped anatomies associated with the current study in order for that historical study to be selected as a comparison study. For example, the fifth comparison rule may require that a mapped anatomy of a historical study match any mapped anatomy of the current study in order for that historical study to be selected as a comparison study and communicated to a user. For example, a current study includes mapped anatomies of A, C and D (where A, C and D each represent a mapped anatomy such as a head, neck or chest). The following historical studies are associated with the listed mapped anatomies:

| Historical Study Number | Mapped Anatomies |
| --- | --- |
| 1 | E, G |
| 2 | A |
| 3 | A, C, D |
| 4 | C, D, E |
| 5 | B |

If the fifth comparison rule requires that a mapped anatomy of a historical study match any mapped anatomy of the current study, then upon application of the rule to the historical studies listed in the table, historical studies numbered 2 (as both studies include "A"), 3 (as both studies include "A" and "C"), and 4 (as both studies include "C") would be selected as comparison studies.

In one embodiment of the present invention, a user selects a single rule to be used in selecting one or more comparison studies, as described above.

In another embodiment of the present invention, a user may select a plurality of rules. For example, a user may select the first and third exemplary rules described above. In such an embodiment, comparison study selection routine 212 applies each rule to a plurality of historical studies stored at database 220. The comparison studies selected by applying each of the selected comparison rules are then communicated from database 220 to display routine 213. In other words, in keeping with the above example, all comparison studies selected by applying the first rule and all comparison studies selected by applying the third rule are communicated to display routine 213.

In another embodiment of the present invention, a plurality of rules may be selected, but only the comparison studies selected by applying the least inclusive comparison rule are communicated from database 220 to display routine 213. FIG. 3 illustrates an example of applying three comparison rules in order to customize a hanging protocol in accordance with an embodiment of the present invention.

FIG. 3 illustrates an exemplary application of three comparison rules in accordance with an embodiment of the present invention. FIG. 3 illustrates a current study 340, a first comparison study 310, a second comparison study 320, a third comparison study 330, a first comparison rule 315, a second comparison rule 325, and a third comparison rule 335. Each comparison rule 315, 325, 335 are represented as encompassing an area representative of all comparison studies. In other words, a comparison rule that encompasses a larger area than another comparison rule thereby includes an image data attribute requirement that matches a larger number of comparison studies (as described above). For example, in FIG. 3, third comparison rule 335 is more inclusive than second comparison rule 325, which is in turn more inclusive than first comparison rule 315.

In an embodiment, first, second and third comparison rules 315, 325, 335 are each equivalent to the first, second and fifth exemplary comparison rules described above. In this way, first comparison rule 315 requires that a selected comparison study include an imaging procedure data attribute that matches an imaging procedure data attribute of current study 340. In addition, second comparison rule 325 requires that a "Body Part Examined" DICOM tag of a comparison study match any "Body Part Examined" DICOM tag of current study 340. In addition, third comparison rule 335 requires that a mapped anatomy data attribute of a selected comparison study matches any mapped anatomy data attribute of current study 340. However, this illustration is not meant in any way to constitute a limitation on the present invention and is provided merely as an example.

In continuing with the example illustrated in FIG. 3, the image data attributes associated with each of historical studies 310, 320, 330 and current study 340 are listed below:

| | Imaging Procedure Data Attribute | Mapped Anatomy(ies) | "Body Part Examined" DICOM Tag |
| --- | --- | --- | --- |
| Current Study 340 | Procedure A | Anatomies A, B | Anatomy A |
| First Historical Study 310 | Procedure A | Anatomies A, B | Anatomy A |
| Second Historical Study 320 | Procedure B | Anatomies A, C, D | Anatomies A, D |
| Third Historical Study 330 | Procedure C | Anatomies B, E | Anatomy E |

When a user selects comparison rules 315, 325, 335, the first, third and fifth exemplary comparison rules (described above) are used by comparison study selection processor 212. Upon applying each of rules 315, 325, 335, comparison study selection processor 212 discovers that applying rule 335 results in all three historical studies 310, 320, 330 being selected as comparison studies (as each historical study 310, 320, 330 includes at least one mapped anatomy that matches current study 340). This result is represented by the area encompassed by rule 335.

The application of rule 325 results in two comparison studies (310 and 320) being selected by comparison study selection processor 212 (as each historical study 310, 320 includes at least one "Body Part Examined" DICOM tag that matches any "Body Part Examined" DICOM tag of current study 340).

The application of rule 315 results in only comparison study 310 being selected as historical study 310 is the only study that includes an imaging procedure image data attribute that matches the imaging procedure image data attribute of current study 340.

As described above, in one embodiment, comparison study selection processor 212 selects one or more historical studies that match each selected rule as comparison studies. For example, in FIG. 3, when all three rules 315, 325, 335 are selected, comparison study selection processor 212 selects and communicates all matching comparison studies 310, 320, 330 to display routine 213.

In another embodiment of the present invention, comparison study selection processor 212 selects one or more comparison studies that match the least inclusive rule of a plurality of selected rules. For example, in FIG. 3, when rules 315, 325, 335 are all selected, comparison study selection processor 212 selects and communicates only historical study 310. As the application of rule 335 results in three historical studies being selected, the application of rule 325 results in two historical studies being selected, and the application of rule 315 results in a single historical study being selected, rule 315 is the least inclusive rule of the selected rules 315, 325, 335.

In another embodiment of the present invention, one or more rules may be incapable of being selected and/or applied with each other. In other words, one or more rules may be mutually exclusive with respect to each other. For example, server 130 and/or display device 140 may include a set of instructions (such as software, for example) that make two or more rules mutually exclusive. In such an embodiment, the set of instructions residing on server 130 and/or display device 140 may prevent a user from selecting the mutually exclusive rules or comparison study selection processor 212 may prevent two or more mutually exclusive rules from being applied. For example, the second, third and fourth exemplary rules discussed above may be mutually exclusive.

Once display device 140 receives one or more selected comparison studies, display device 140 may automatically populate or present a display screen or a subdivision of a display screen with a list of the selected comparison study (ies). A user may then select a comparison study to be presented at display device 140.

In another embodiment of the present invention, once display device 140 receives one or more selected comparison studies, display device 140 may automatically populate or present a display screen or a subdivision of a display screen with the selected comparison study(ies). No user interaction is required in this embodiment to present a comparison study.

Once one or more comparison studies have been selected and presented to a user, the user may select a new comparison rule or a new set of comparison rules. Rule selection routine 211 may monitor an input device of display device 140 and determine whether a user has selected additional rules, as described above. If new rules are selected, the rules may be communicated to comparison study selection routine 212. Comparison study selection routine 212 may then select the appropriate comparison studies (based on the newly selected rule(s), as described above) and communicate them to display routine 213.

FIG. 4 illustrates a flowchart for a method 400 for rule-based comparison study matching to customize a hanging protocol in accordance with an embodiment of the present invention. First, at step 410, a current study of image(s) is selected, as described above. For example, a current study of image(s) may be communicated from database 220 in server 130 to one or more display devices 140.

Next, at step 420, one or more comparison rules are selected, as described above. For example, a user may select one or more rules using an input device connected to display device 140. Once the comparison rule(s) is(are) selected, the rule(s) is(are) communicated to a rule selection routine 211, as described above.

Next, at step 430, the selected rule(s) are communicated to a comparison study selection routine or processor 212, as described above.

Next, at step 440, the selected rule(s) is(are) then applied to a plurality of historical studies in order to select one or more comparison studies, as described above. The rule(s) is(are) applied to a plurality of historical studies by comparing one or more image data attributes of each historical study with at least one of an image data attribute requirement of the rule(s) and an image data attribute of a current study, as described above.

Next, at step 450, one or more historical studies are selected as comparison studies based at least in part on the application of one or more rules at step 440, as described above. In one embodiment of the present invention, if more than one comparison rule is selected, then all historical studies that match or satisfy the requirement(s) of each of the selected rules are selected as comparison studies. That is, if applying a first rule results in 2 comparison studies being selected and applying a second rule results in 4 comparison studies being selected, then all 6 comparison studies are selected at step 450.

In another embodiment of the present invention, at step 450, when a plurality of comparison rules is selected at step 420, then only the historical studies satisfying the requirements of the least inclusive comparison rule are selected as comparison studies, as described above. In other words, if applying a first comparison rule results in 2 comparison studies being selected and applying a second comparison rule results in 4 comparison studies being selected, then only the 2 comparison studies (selected by applying the first comparison rule) are selected at step 450.

Next, at step 460, the selected comparison study(ies) is(are) communicated to a display device 140, as described above. Next, at step 470, the selected comparison study(ies) is(are) presented or populated on display device 140, as described above. In one embodiment of the present invention, the selected comparison study(ies) is(are) presented at step 470 by presenting a user with a list of the selected comparison study(ies) on display device 140. The user may then select one or more of the selected comparison studies from the list to be displayed on display device 140.

In another embodiment of the present invention, the selected comparison study(ies) is(are) automatically presented at step 470 without any required user interaction, as described above.

Next, at step 480, rule selection routine 211 determines if a user has selected new or additional comparison rules. If a user has selected additional rules, method 400 proceeds to step 430, where the newly selected rules are communicated to comparison study selection routine 212, as described above. If the user has not selected any additional rules, method 400 terminates.

While particular elements, embodiments and applications of the present invention have been shown and described, it is understood that the invention is not limited thereto since modifications may be made by those skilled in the art, particularly in light of the foregoing teaching. It is therefore contemplated by the appended claims to cover such modifications and incorporate those features that come within the spirit and scope of the invention.

What is claimed is:

1. A method for presenting at least one medical imaging study in a Picture Archiving and Communication System ("PACS"), said method including using a processor to implement steps of:
    applying a plurality of comparison rules that can identify plurality of comparison imaging studies, each comparison rule comparing at least one image data attribute associated with a current imaging study with at least one image data attribute associated with each of a plurality of historical studies, said current imaging study and each of said plurality of historical studies including at least one image;
    Selecting one or more historical studies that match each comparison rule of the plurality of comparison rules as the plurality of comparison imaging studies;
    identifying a least inclusive comparison rule of the plurality of comparison rules, the least inclusive comparison rule providing a lowest number of comparison imaging studies from the plurality of historical imaging studies; and
    selecting one or more comparison imaging study that matches the least-inclusive comparison rule.

2. The method of claim 1, further including presenting said at least one comparison study at a display device.

3. The method of claim 1, wherein said at least one image data attribute associated with said current study and said at least one image data attribute associated with said at least one historical study each includes data representative of at least one of:
    an imaging procedure used to obtain said at least one image of said current study or said at least one historical study, respectively;
    one or more Digital Imaging and Communications in Medicine ("DICOM") tags representative of one or more anatomies examined in said current study or said at least one historical study, respectively; and
    one or more mapped anatomies of said current study or said at least one historical study, respectively.

4. The method of claim 3, wherein said selecting step includes selecting said at least one comparison study if said imaging procedure associated with said at least one comparison study matches said imaging procedure associated with said current study.

5. The method of claim 3, wherein said selecting step includes selecting said at least one comparison study if any of said DICOM tags associated with said at least one comparison study match at least one of said DICOM tags associated with said current study.

6. The method of claim 3, wherein said selecting step includes selecting said at least one comparison study if any of said mapped anatomies associated with said at least one comparison study match at least one anatomy in a set of said mapped anatomies.

7. The method of claim 6, wherein said set of said mapped anatomies is defined by a user of said PACS.

8. The method of claim 3, wherein said selecting step includes selecting said at least one comparison study if said imaging procedure associated with said at least one comparison study matches at least one imaging procedure in a set of imaging procedures.

9. The method of claim 8, wherein said set of imaging procedures is defined by a user of said PACS.

10. The method of claim 3, wherein said selecting step includes selecting said at least one comparison study if any of said mapped anatomies associated with said at least one comparison study match at least one of said mapped anatomies associated with said current study.

11. A computer-readable storage medium including a set of instructions for a computer, said instructions including:
    a rule selection routine configured to monitor a selection of a plurality of comparison rules used to identify plurality of comparison imaging studies, said plurality of comparison rules used to compare at least one image data attribute associated with a current imaging study with at least one image data attribute associated with each of a plurality of historical studies, said current study and said plurality of historical studies each including at least one image; and
    a comparison study selection routine configured to select one or more historical studies that match each comparison rule of the plurality of comparison rules as the plurality of comparison imaging studies, and identify a least inclusive comparison rule of the plurality of comparison rules, the least inclusive comparison rule providing a lowest number of comparison imaging studies from the plurality of historical imaging studies, the comparison study selection routine configured to select one or more comparison imaging study that matches the least-inclusive comparison rule.

12. The set of instructions of claim 11, further including a display routine configured to present said current study and said at least one comparison study at a display device.

13. The set of instructions of claim 11, wherein said at least one image data attribute associated with said current study and said at least one image data attribute associated with each of said plurality of historical studies each includes data representative of at least one of:
    an imaging procedure used to obtain said at least one image of said current study or said historical study, respectively;
    one or more Digital Imaging and Communications in Medicine ("DICOM") tags representative of one or more anatomies examined in said current study or said historical study, respectively; and
    one or more mapped anatomies of said current study or said historical study, respectively.

14. The set of instructions of claim 11, wherein said plurality of rules is stored on at least one of said display workstation and a network server associated with a Picture Archiving and Communication System ("PACS"), said least-inclusive rule of said plurality of employed to select said at least one comparison study from said plurality of historical studies stored at said network server.

15. The set of instructions of claim 13, wherein said comparison study selection routine is configured to select said at least one comparison study if said imaging procedure associated with said at least one comparison study matches said imaging procedure associated with said current study.

16. The set of instructions of claim 13, wherein said comparison study selection routine is configured to select said at least one comparison study if any of said DICOM tags match at least one of said DICOM tags associated with said current study.

17. The set of instructions of claim 13, wherein said comparison study selection routine is configured to select said at least one comparison study if any of said mapped anatomies associated with said at least one comparison study match at least one mapped anatomy in a set of said mapped anatomies.

18. The set of instructions of claim 17, wherein said set of said mapped anatomies is defined by a user.

19. The set of instructions of claim 13, wherein said comparison study selection routine is configured to select said at least one comparison study if said imaging procedure associated with said at least one comparison study matches at least one of a set of imaging procedures.

20. The set of instructions of claim 19, wherein said set of imaging procedures is defined by a user.

21. The set of instructions of claim 13, wherein said comparison study selection routine is configured to select said at least one comparison study any of said mapped anatomies associated with said at least one comparison study matches any of said mapped anatomies associated with said current study.

22. A system for presenting at least one medical imaging study at a display workstation in a Picture Archiving and Communication System ("PACS"), said system including:
   a computer-readable storage medium configured to store a plurality of comparison rules used to identify plurality of comparison imaging studies, each of said plurality of comparison rules used to compare at least one image data attribute associated with a current imaging study with at least one image data attribute associated with each of a plurality of historical studies, said current imaging study and said plurality of historical studies each including at least one image; and
   a comparison study selection processor configured to select one or more historical studies that match each comparison rule of the plurality of comparison rules as the plurality of comparison imaging studies, and identify a least inclusive comparison rule of the plurality of comparison rules, the least inclusive comparison rule providing a lowest number of comparison imaging studies from the plurality of historical imaging studies, the comparison study selection routine configured to select one or more comparison imaging study that matches the least-inclusive comparison rule.

23. The system of claim 22, wherein said at least one image data attribute associated with said current study and each of said plurality of historical studies includes at least one of:
   an imaging procedure used to obtain said at least one image of said current study or said historical study, respectively;
   one or more Digital Imaging and Communications in Medicine ("DICOM") tags representative of one or more anatomies examined in said current study or said historical study, respectively; and
   one or more mapped anatomies of said current study or said historical study, respectively.

24. The system of claim 22, wherein said plurality of rules includes:
   a first rule requiring that an imaging procedure associated with said at least one comparison study match an imaging procedure associated with said current study;
   a second rule requiring that at least one Digital Imaging and Communications in Medicine ("DICOM") tag associated with said at least one comparison study matches at least one of said DICOM tags associated with said current study;
   a third rule requiring that said imaging procedure associated with said at least one comparison study matches at least one imaging procedure in a set of imaging procedures; and
   a fourth rule requiring that at least one mapped anatomy associated with said at least one comparison study matches at least one of said mapped anatomies associated with said current study.

25. The system of claim 24, wherein said fourth rule requires that at least one of said mapped anatomies associated with said at least one comparison study matches at least one mapped anatomy in a set of said mapped anatomies.

26. The system of claim 25, wherein said set of said mapped anatomies is defined by a user.

27. The system of claim 24, wherein said set of imaging procedures is defined by a user.

28. The system of claim 24, wherein said comparison study selection processor is configured to select said at least one comparison study by comparing said at least one image data attribute associated with said current study with said at least one image data attribute associated with each of said plurality of historical studies in accordance with said plurality of rules, said rules employed by said comparison study selection processor in an order progressing from said least-inclusive rule to a most-inclusive rule,
   wherein said most-inclusive rule provides for a selection of more of said comparison studies than said least-inclusive rule when employed by said comparison study selection routine.

* * * * *

UNITED STATES PATENT AND TRADEMARK OFFICE
CERTIFICATE OF CORRECTION

PATENT NO.       : 7,634,121 B2
APPLICATION NO.  : 11/070104
DATED            : December 15, 2009
INVENTOR(S)      : Novatzky et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1106 days.

Signed and Sealed this

Ninth Day of November, 2010

David J. Kappos
*Director of the United States Patent and Trademark Office*